US007109346B2

(12) United States Patent
Beller et al.

(10) Patent No.: US 7,109,346 B2
(45) Date of Patent: Sep. 19, 2006

(54) N-PHENYL-PYRROL BISPHOSPHANE COMPOUNDS AND THE METAL COMPLEXES OF THE SAME

(75) Inventors: Matthias Beller, Nienhagen (DE); Ralf Jackstell, Cuxhaven (DE); Holger Klein, Rostock (DE); Detlef Heller, Dettmannsdorf (DE); Hans-Joachim Drexler, Rostock (DE); Klaus-Diether Wiese, Haltern am See (DE); Dirk Roettger, Recklinghausen (DE)

(73) Assignee: OXENO Olefinchemie GmbH & Co. KG, Marl (DE)

( * ) Notice: Subject to any disclaimer, the term of this patent is extended or adjusted under 35 U.S.C. 154(b) by 330 days.

(21) Appl. No.: 10/451,631

(22) PCT Filed: Dec. 12, 2001

(86) PCT No.: PCT/EP01/14619

§ 371 (c)(1),
(2), (4) Date: Jan. 20, 2004

(87) PCT Pub. No.: WO02/055528

PCT Pub. Date: Jul. 18, 2002

(65) Prior Publication Data

US 2004/0116713 A1 Jun. 17, 2004

(30) Foreign Application Priority Data

Jan. 10, 2001 (DE) ................................ 101 00 708

(51) Int. Cl.
*C07F 9/28* (2006.01)

(52) U.S. Cl. ...................................................... 548/111

(58) Field of Classification Search ................. 548/111
See application file for complete search history.

(56) References Cited

U.S. PATENT DOCUMENTS 6,077,958 A * 6/2000 Antognazza et al. ........ 548/101
6,153,758 A * 11/2000 Sannicolo et al. .......... 548/111
6,229,019 B1 * 5/2001 Nakamoto et al. .......... 548/110
6,586,357 B1 * 7/2003 Antognazza et al. ........ 502/162
6,627,758 B1 * 9/2003 Grotjahn ..................... 548/101

FOREIGN PATENT DOCUMENTS

| | | |
|---|---|---|
| EP | 0 104 375 | 4/1984 |
| WO | 92/16536 | 10/1992 |
| WO | 99/52915 | 10/1999 |

OTHER PUBLICATIONS

Xuedong Dai, et al., "Synthesis of 2-heterosubstituted quinazolinone atropisomeric phosphine ligands by direct lithiation of a 2-unsubsituted quinazolinone system", Tetrahedron: Asymmetry, vol. 10, No. 1, pp. 25-29.

Hans-Joachim Drexler, et al., "Part lll, COD versus NBD precatalysts. Dramatic difference in the asymmetric hydrogenation of prochiral olefins with five-membered diphosphine Rh-hydrogenation catalysts", Journal of Organometallic Chemistry, vol. 612, No. 1-2, pp. 89-102, Mar. 1, 2001.

* cited by examiner

*Primary Examiner*—Deborah C. Lambkin
(74) *Attorney, Agent, or Firm*—Oblon, Spivak, McClelland, Maier & Neustadt, P.C.

(57) ABSTRACT

N-Phenylpyrrolebisphosphines of the formula I (I)

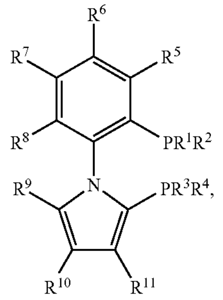

metal complexes of these N-phenylpyrrolebisphosphines and their use in metal-catalyzed reactions.

17 Claims, No Drawings

N-PHENYL-PYRROL BISPHOSPHANE COMPOUNDS AND THE METAL COMPLEXES OF THE SAME

The present invention relates to N-phenylpyrrolebisphosphines and their metal complexes, to their preparation and to their use in catalytic reactions.

Phosphorus compounds as ligands for metals in catalytic reactions have been known for some time. The type of ligand can be used to influence activity and selectivities (chemoselectivity, regioselectivity, diastereoselectivity, enantioselectivity, etc.) within a wide range. Bidentate ligands are often far superior to monodentate ligands.

For instance, U.S. Pat. Nos. 4,694,109 and 4,879,416 describe bisphosphine ligands and their use in the hydroformylation of olefins at low synthesis gas pressures. Especially in the hydroformylation of propene, ligands of this type allow high activities and high n/i selectivities to be achieved. WO 95/30680 discloses bidentate phosphine ligands and their use in catalysis, in hydroformylation reactions among others. Ferrocene-bridged bisphosphines are described, for example, in the patents U.S. Pat. Nos. 4,169,861, 4,201,714 and 4,193,943 as ligands for hydroformylations.

In asymmetric hydrogenations, chiral bisphosphines are used very successfully in many cases. A known example is the ligand BINAP (2,2'-bis(diphenylphosphino)-1,1'-binaphthyl) which is even commercially obtainable. This ligand has also been used in many other metal-catalyzed reactions, for example in the Heck reaction.

The technical literature includes a variety of publications which describe the use of ligands in conjunction with metals as catalysts. A good review of the current state of the field of use for transition metal catalysts in organic synthesis can be found in Matthias Beller, Carsten Bolm (Ed.), "Transition Metals for Organic Synthesis", Wiley-VCH, Weinheim, New York, Chichester, Brisbane, Singapore, Toronto, 1998, Vol. 1&2. Examples of catalysts and their fields of use, common industrial scale processes, etc., can be found in B. Cornils, W. A. Herrmann (Ed.), "Applied Homogeneous Catalysis with Organometallic Compounds", VCH, Weinheim, New York, Basle, Cambridge, Tokyo, 1996, Vol. 1&2.

Despite the wealth of existing systems, there are no "standard solutions" for metal-catalyzed reactions. The conditions have to be newly optimized for each substrate and reaction. In addition, some ligands are relatively difficult to synthesize, so that their use in industrial processes is not viable.

There is therefore a need for further easily accessible ligand systems for metal-catalyzed reactions.

It has been found that N-phenylpyrrolebisphosphines of the general structure I (I)

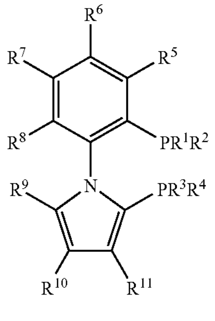

can be prepared in a simple manner and are suitable as ligands in metal-catalyzed reactions.

The present invention therefore provides N-phenylpyrrolebisphosphines of the general formula I (I)

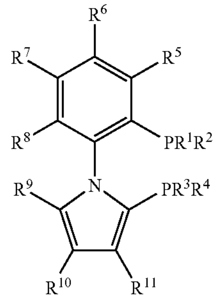

where $R^1$, $R^2$, $R^3$, $R^4$=aliphatic, cycloaliphatic or aromatic hydrocarbon radicals having from 1 to 25 carbon atoms, and $R^1$ and $R^2$ and/or $R^3$ and $R^4$ may be joined by one or more covalent bonds, $R^5$, $R^6$, $R^7$, $R^8$, $R^9$, $R^{10}$, $R^{11}$=H, aliphatic, alicyclic, aliphatic-alicyclic, heterocyclic, aliphatic-heterocyclic, aromatic, aromatic-aromatic, aliphatic-aromatic hydrocarbon radicals having from 1 to 50 carbon atoms, and $R^5$ to $R^{11}$ may each be defined identically or differently and be covalently joined together, and each be F, Cl, Br, I, $—CF_3$, $—OR^{12}$, $—COR^{12}$, $—CO_2R^{12}$, $—CO_2M$, $—SR^{12}$, $—SO_2R^{12}$, $—SOR^{12}$, $—SO_3R^{12}$, $—SO_3M$, $—SO_2NR^{12}R^{13}$, $NR^{12}R^{13}$, $N^+R^{12}R^{13}R^{13}$, $N{=}CR^{12}R^{13}$, $NH_2$, where $R^{12}$, $R^{13}$=H, substituted or unsubstituted, aliphatic or aromatic hydrocarbon radicals having from 1 to 25 carbon atoms, each defined identically or differently, and M=alkali metal, alkaline earth metal, ammonium, phosphonium ion.

Specific embodiments of the N-phenylpyrrolebisphosphines according to the invention relate to phosphines of the formulae II, III, IV and V (II)

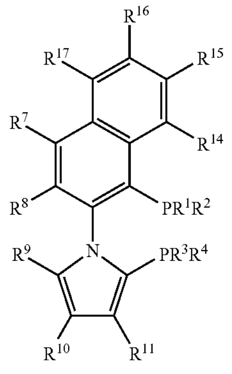

-continued (III)

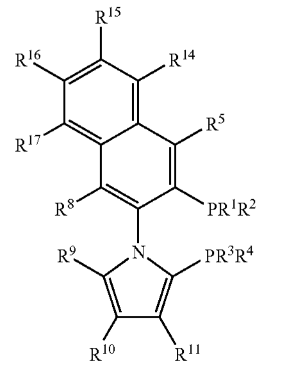

(IV)

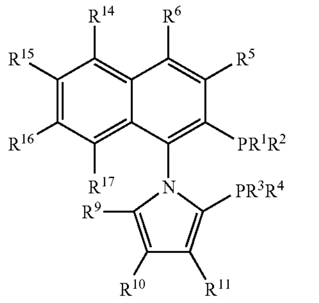

(V)

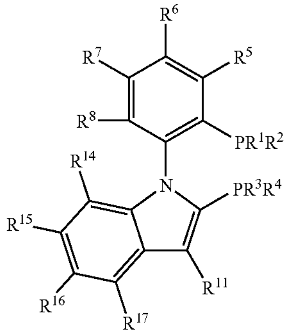

where each of the radical pairs $R^5$ and $R^6$, $R^6$ and $R^7$, $R^7$ and $R^8$ or $R^9$ and $R^{10}$ together are a fused aromatic which is optionally likewise substituted.

The substituents of the additional aromatic system $R^{14}$, $R^{15}$, $R^{16}$ and $R^{17}$ may each be H, an aliphatic, alicyclic, aliphatic-alicyclic, heterocyclic, aliphatic-heterocyclic, aromatic, aromatic-aromatic, aliphatic-aromatic hydrocarbon radical having from 1 to 50 carbon atoms, and $R^{14}$ to $R^{17}$ may each be defined identically or differently and be covalently joined together, and each be F, Cl, Br, I, $-Si(CH_3)_3$, $-CF_3$, $-OR^{12}$, $-COR^{12}$, $-CO_2R^{12}$, $-CO_2M$, $-SR^{12}$, $-SO_2R^{12}$, $-SOR^{12}$, $-SO_3R^{12}$, $-SO_3M$, $-SO_2NR^{12}R^{13}$, $NR^{12}R^{13}$, $N^+R^{12}R^{13}R^{13}$, $N{=}CR^{12}R^{13}$, $NH_2$, where $R^{12}$, $R^{13}$=H, substituted or unsubstituted, aliphatic or aromatic hydrocarbon radicals having from 1 to 25 carbon atoms, each defined identically or differently, and M=alkali metal, alkaline earth metal, ammonium, phosphonium ion.

$R^1$, $R^2$, $R^3$, $R^4$, $R^5$, $R^6$, $R^7$, $R^8$, $R^9$, $R^{10}$ and $R^{11}$ in the formulae II, III, IV and V are as defined in claim 1 or for formula I, and $R^1$ to $R^4$ and $R^5$ to $R^{11}$ may in each case be defined identically or differently.

The aliphatic, cycloaliphatic or aromatic hydrocarbon radicals may contain heteroatoms, for example nitrogen, oxygen or sulfur, and optionally bear one or more substituents, for example halogen atoms. Examples of $R^1$–$R^4$ are phenyl, m-sulfonatophenyl, p-fluorophenyl, o-fluorophenyl, m-fluorophenyl, p-methoxyphenyl, o-methoxyphenyl, m-methoxyphenyl, 1-naphthyl, 2-naphthyl, methyl, ethyl, n-propyl, i-propyl, n-butyl, s-butyl, i-butyl, hexyl, cyclohexyl, adamantyl. Examples in which $R^1$ and $R^2$ and/or $R^3$ and $R^4$ have one or more covalent bonds are 1,1'-diphenyl-2,2'-diyl, cyclooctane-1,5-diyl. $R^1$ to $R^4$ are preferably substituted or unsubstituted phenyl, cyclohexyl and adamantyl groups.

When the rotation around the N-phenyl bond is restricted, some of the compounds according to the invention are enantiomers as a consequence of axial chirality, and, in the event of additional chirality in the radicals $R^1$–$R^{11}$, diastereomers.

In preferred embodiments of the invention, the N-phenylpyrrolebisphosphines are chiral, and preference is given to one or more of the radicals $R^1$ to $R^{11}$ being chiral. Particular preference is given to chiral substituents for $R^1$–$R^4$. Examples of such chiral groups are menthyl, camphyl, 1,1'-binaphth-2-yl, hexane-2,5-diyl.

The use of one or more chiral radicals in $R^1$ to $R^{11}$ offers the advantage, inter alia, that when there is axial chirality (N-phenyl bond as the chirality axis), the diastereomers can be easily separated.

The invention therefore relates both to mixtures of individual enantiomers and diastereomers of the N-phenylpyrrolebisphosphine ligands according to the invention and to the individual enantiomers or diastereomers themselves and their use in enantioselective or diastereoselective catalytic reactions.

The present invention further provides N-phenylpyrrolebisphosphine-metal complexes containing a transition group metal of the 1st, 2nd, 3rd, 4th, 5th, 6th, 7th or 8th transition group of the Periodic Table, the elements of the lanthanides and/or actinides and one or more N-phenylpyrrolebisphosphines of the formulae I, II, III, IV or V. The substituents ($R^1$–$R^{17}$) of these N-phenylpyrrolebisphosphines are as already defined. Metals used with preference are Ti, Zr, Cr, Mo, W, Mn, Re, Fe, Ru, Os, Co, Rh, Ir, Ni, Pd, Pt, Cu, Ag and Zn. Particular preference is given to the metals of the 8th transition group of the Periodic Table.

The remarks of all embodiments of the N-phenylpyrrolebisphosphines of the formulae I to V apply correspondingly to the metal complexes. When the N-phenylpyrrolebisphosphine ligands are chiral as described, the metal complexes may have one, more than one or exclusively chiral N-phenylpyrrolebisphosphine ligands.

Representative examples of ligands of the general formulae I, II, III, IV and V for the purposes of this invention are depicted hereinbelow, without limiting the scope of protection of the present invention.

I-a
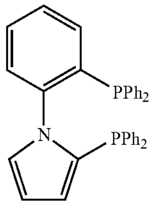
I-b
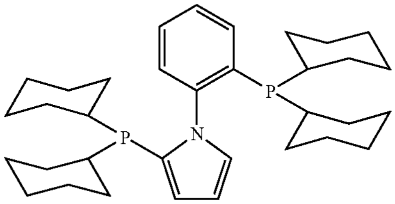
I-c
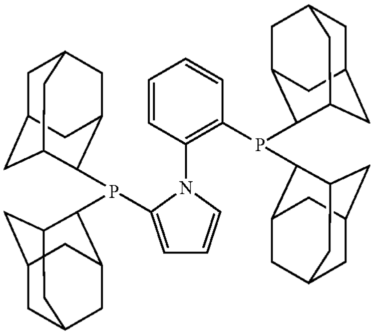
I-d
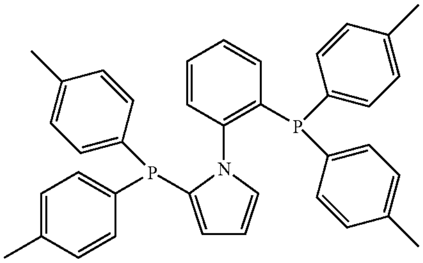
I-f
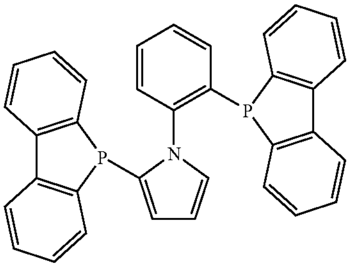
I-g
-continued
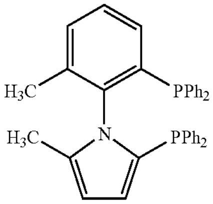
I-h
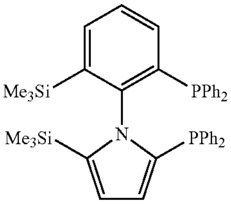
I-i
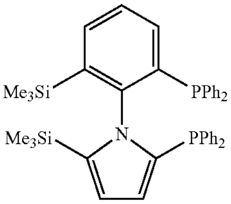
I-j
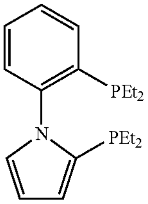
I-k
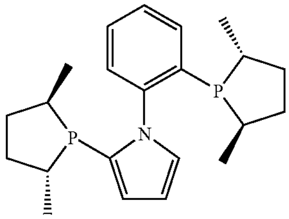
II-a
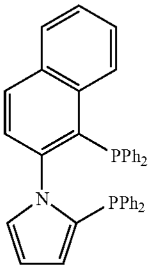
III-a -continued
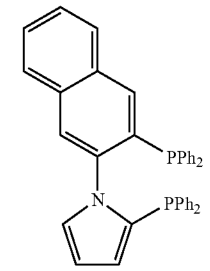
IV-a
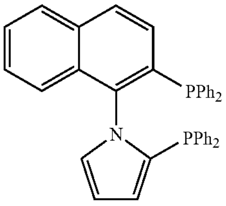
IV-b
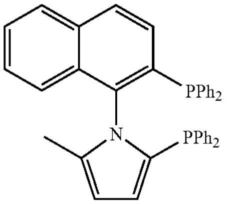
IV-c
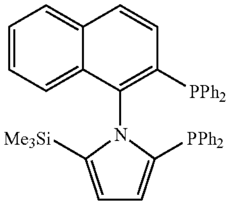
V-a
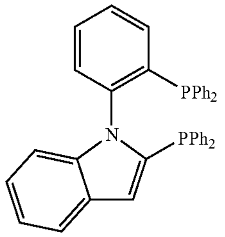
V-b
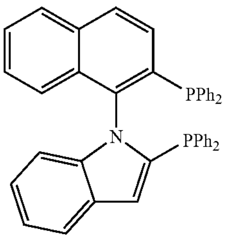
V-c
-continued
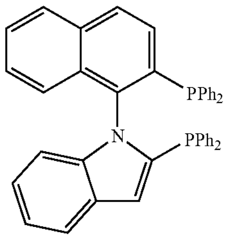
V-d
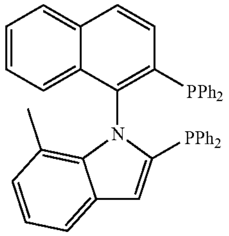
The N-phenylpyrrolebisphosphines according to the invention can be obtained by various synthetic routes. A simple route is the double metalation of N-phenylpyrroles and the subsequent reaction with the phosphorus component ($R^3$=$R^1$, $R^4$=$R^2$).
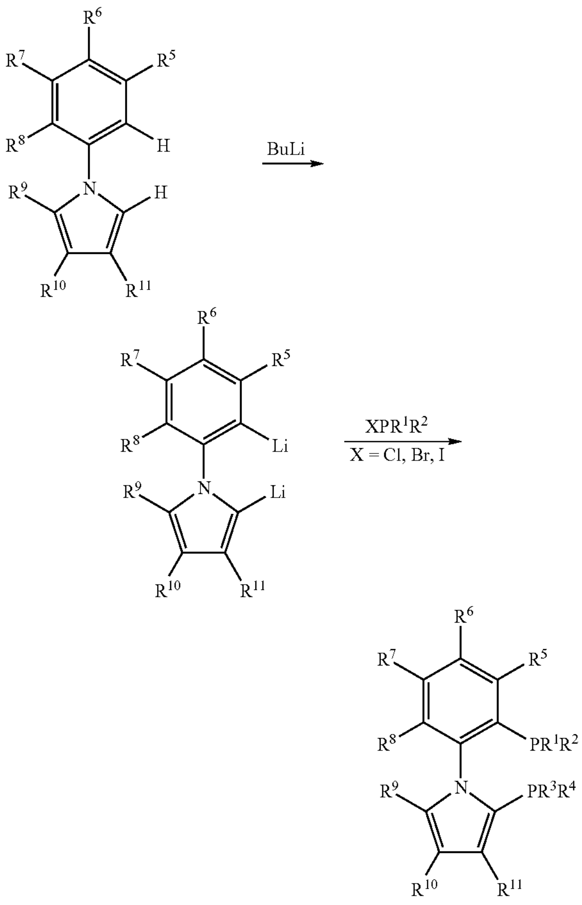

The radicals $R^5$–$R^{11}$ can be introduced even after attachment of the phosphorus groups. This route was taken, for example, in the synthesis of compound I-h:

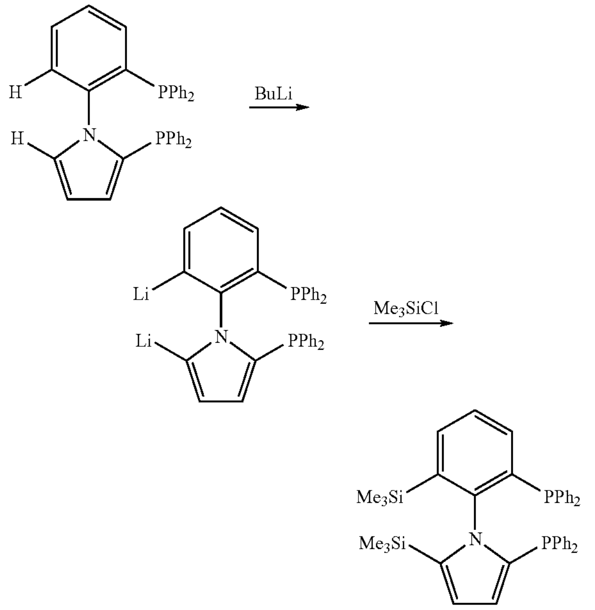

Ligands occurring in racemic form can be separated into the optical isomers by literature routes, for example chromatographically on chiral supports or as diastereomers after reaction with chiral auxiliaries and subsequent dissociation.

The N-phenylpyrrolebisphosphines according to the invention of the formulae I, II, III, IV and V are notable for a high hydrolysis stability. They are especially soluble in the common organic solvents. When one or more groups R1 to R11 or R14 to R17 or one or more substituents R1 to R4 bears a strongly polar radical (for example a sulfonic acid group), the solubility falls in nonpolar organic solvents, while at the same time rising in polar solvents, for example water. The N-phenylpyrrolebisphosphines according to the invention and their metal complexes may therefore be soluble even in water or polar organic solvents.

As a consequence of their high molecular weight, the N-phenylpyrrolebisphosphines according to the invention have a low volatility. They can therefore easily be removed from more volatile reaction products.

The invention further provides the use of the N-phenylpyrrolebisphosphines or their metal complexes in hydrogenations, isomerizations, carbonylations, carboxylations, hydroformylations, hydrocyanations, cyclopropanations, C—C couplings, oligomerizations or polymerizations.

The N-phenylpyrrolebisphosphines according to the invention of the formulae I, II, III, IV and V are suitable building blocks for the preparation of complexes with metals of the 1st to 8th transition group of the Periodic Table, the lanthanides and/or the actinides. Especially with metals of the 6th to 8th transition group, these complexes can be used as catalysts for hydrogenations, isomerizations, carbonylations, carboxylations, hydroformylations, hydrocyanations, cyclopropanations, C—C coupling reactions, oligomerizations and polymerizations. Preferred fields of use are hydrogenations, hydroformylations and C—C coupling reactions.

When the N-phenylpyrrolebisphosphines according to the invention of the formulae I to V are used, optionally as the metal complex, in hydrogenations, preference is given to using metals of the 8th transition group of the Periodic Table. The substrates used are preferably compounds having double bonds, for example C═C, C═O or C═N double bonds which are hydrogenated to a single bond. Examples of hydrogenations can be found, for example, in Matthias Beller, Carsten Bolm (Ed.) "Transition Metals for Organic Synthesis", Wiley-VCH, Weinheim, New York, Chichester, Brisbane, Singapore, Toronto, 1998, Vol. 2, pages 3–80.

When the N-phenylpyrrolebisphosphines according to the invention of the formulae I to V are used, optionally as a metal complex, in hydroformylations, preference is given to using metals of the 8th transition group of the Periodic Table. Especially when rhodium is used as the catalyst metal, high catalytic activities are obtained in the hydroformylations. The reactants used in these hydroformylations are preferably olefins having from 2 to 25 carbon atoms, for example butenes (1-butene, 2-butene, i-butene), octenes (1-octene, dibutenes), dodecenes (tributenes).

When the N-phenylpyrrolebisphosphines according to the invention of the formulae I to V are used, optionally as the metal complex, in C—C coupling reactions, preference is given to using metals of the 8th transition group of the Periodic Table, more particularly of nickel and palladium. Examples of C—C coupling reactions can be found, for example, in Matthias Beller, Carsten Bolm (Ed.) "Transition Metals for Organic Synthesis", Wiley-VCH, Weinheim, New York, Chichester, Brisbane, Singapore, Toronto, 1998, Vol. 1, pages 208–240.

In the metal-catalyzed reactions, either the N-phenylpyrrolebisphosphine-metal complexes, optionally with additional, free ligand, or the N-phenylpyrrolebisphosphines and a metal compound from which the catalyst complex forms with the N-phenylpyrrolebisphosphines under the reaction conditions are used.

When the N-phenylpyrrolebisphosphine compounds according to the invention and/or their metal complexes are used in metal-catalyzed reactions, the ratio of ligand to metal (mol/mol) is from 1:2 to 200:1, preferably from 1:1 to 1:50, more preferably from 1:1 to 1:20. Ligand or ligand-metal complex are generally dissolved homogeneously in one or more of the liquid phases present. It is also possible to use the N-phenylpyrrolebisphosphines in supported aqueous phase catalysts.

The examples which follow are intended to illustrate the invention, but not to restrict the scope of application as evident from the patent claims.

EXAMPLES

All operations are carried out under argon by means of Schlenk techniques with dried and degassed solvents.

Example 1

1-(2-Diphenylphosphinophenyl)pyrrole-2-diphenylphosphine (I-a, JaPHOS)

1.52 g (10.6 mmol) of N-phenylpyrrole are dissolved in 50 ml of $Et_2O$ in a 250 ml three-neck flask (equipped with magnetic stirring) and admixed with 2.5 g (3.2 ml) of TMEDA (tetramethylethylenediamine). At 25° C., 13.6 ml of 1.6 molar n-butyllithium solution (21.2 mmol) are subsequently added. The reaction mixture is stirred at room temperature for 12 h. This reaction solution I is transferred to a dropping funnel. 4.68 g (21.23 mmol) of diphenylchlorophosphine are mixed with 50 ml of ether in a 250 ml three-neck flask. This solution II is cooled to 0° C. Solution I of the dilithiated N-phenylpyrrole is slowly added dropwise at 20° C. to this solution II. Stirring is subsequently continued at room temperature for 1 h. The reaction solution is admixed with 20 ml of water and stirred for 10 min. The phases are separated and the organic phase is dried over sodium sulfate for 12 h. This is subsequently concentrated under reduced pressure and the residue is dissolved in 20 ml of toluene. This solution is cautiously covered with 100 ml of hexane. The target product crystallizes out within one day. It is filtered and dried under reduced pressure.

Yield: 4.88 g (90% of theory); M=511.54 g/mol $^{31}$P NMR:(δ[ppm], J[Hz], $CDCl_3$): −17.5 d, $J_{PP}$=18; −30.7 d, $J_{PP}$=18

$^{1}$H NMR: (δ[ppm], J[Hz], $CDCl_3$): 6.01 d,d, J=3.6, J=3.6 (1H); 6.11 d, d, J=3.57, J=3.57 (1H); 6.58 m (1H), 7.0 m(4H); 7.1–7.3 m (20H)

$^{13}$C NMR: (δ[ppm], J[Hz], $CDCl_3$): 108.9 s; 118.9 s; 128–129 m; 130.0 d, J=3; 133–134 m; 34.8 d, J=2.8; 136.9 s; 137.0 d, J=2; 137.3 d, J=13.3; 137.7 d, $^{1}J_{PC}$=17.16; 137.8 d, $^{1}J_{PC}$=15.2; 144.4 d, $^{1}J_{PC}$=26; 144.7 d, $^{1}J_{PC}$=26

MS, m/z (%): 511(1)[$M^+$], 434(7)[$M^+$-Ph], 326(100)[$M^+$-$PPh_2$], 249(10)[$M^+$-$PPh_2$-Ph], 183(15)[$PPh_2$], 172(8)[$M^+$-$PPh_2$-2Ph]; EA: calc.: C:79.8, H:5.32, N:2.7; found: C:79.9, H:5.5, N:2.5.

Example 2

1-(2-Dicyclohexylphosphinophenyl)pyrrole-2-dicyclohexylphosphine (I-b, Cyc-JaPHOS)

0.43 g (3.04 mmol) of N-phenylpyrrole are dissolved in 20 ml of $Et_2O$ in a 50 ml three-neck flask (equipped with magnetic stirring) and admixed with 0.704 g (0.91 ml) of TMEDA (tetramethylethylenediamine). At 25° C., 3.8 ml of 1.6 molar n-butyllithium solution (6.06 mmol) are subsequently added. The reaction mixture is stirred at room temperature for 12 h. This reaction solution I is transferred to a dropping funnel. 1.41 g (6.06 mmol) of dicyclohexylchlorophosphine are mixed with 20 ml of $Et_2O$ in a 100 ml three-neck flask. This solution II is cooled to 0° C. Solution I of the dilithiated N-phenylpyrrole is added dropwise at 0° C. to the solution II. The mixture is subsequently stirred at 25° C. for 1 h. The reaction solution is admixed with 20 ml of water and stirred for 10 min. The phases are separated and the organic phase is dried over sodium sulfate for 12 h. This is subsequently concentrated under reduced pressure and the residue is dissolved in 200 ml of hot ethanol. The target product crystallizes out within one day. It is filtered and dried under reduced pressure.

Yield: 1.2 g (74% of theory); M=535.73 g/mol $^{31}$P NMR:(δ[ppm], J[Hz], $CDCl_3$): 15.9 d, $J_{PP}$=6.94; −28.1 d, $J_{PP}$=6.94

$^{1}$H NMR: (δ[ppm], J[Hz], $CDCl_3$): 0.9–1.2 m(21H); 1.5–1.8 m (23H); 6.27 d,d, J=2.57, J=2.58 (1H); 6.45 d,d, J=1.59, J=1.58(1H); 6.7 m(1H); 7.1 m(1H); 7.2–7.3 m(2H); 7.4–7.5 m (1H)

$^{13}$C NMR: (δ[ppm], J[Hz], $CDCl_3$): 26.4 d, J=10.5; 26.7 d, J=8.6; 27.0–27.6 m; 28.6 d, J=5.8; 29.7 d, J=11.4; 29.8 d, J=15; 30.5 d, J=19; 30.9, 31 d,d J=15; 31.4, 31.45 d,d, J=16; 34.6 d, J=26.7; 34.8 d, J=19.1; 35.4 d, J=9.54; 36.1 d, J=16.2; 107.6 s; 116 d, J=3.8; 127 s; 127.5 s; 128.1 s; 129.5 d, J=6.7; 130.0 d,d, J=3.8; 133.0 d, J=3.8; 135.4 d, $^{1}J_{PC}$=22; 147.01, 147.0 d,d, $^{1}J_{PC}$=24.8

MS, m/z (%): 535 (2)[$M^+$], 452 (100) [$M^+$-Cy], 369 (7) [$M^+$-2Cy], 338(5)[$M^+$-$PCy_2$], 204 (7)[$M^+$-4Cy]; 83 (5)[Cy], EA: calc.: C:76.2, H:9.6, N:2.6; found: C:75.9, H:9.5, N:2.6.

Example 3

1-(2-Diadamantylphosphinophenyl)pyrrole-2-diadamantylphosphine (I-c, Ad-JaPHOS)

0.32 g (2.2 mmol) of N-phenylpyrrole are dissolved in 20 ml of $Et_2O$ in a 50 ml three-neck flask (equipped with magnetic stirring) and admixed with 0.5 g (0.75 ml) of TMEDA (tetramethylethylenediamine). At 25° C., 2.8 ml of 1.6 molar n-butyllithium solution (4.4 mmol) are subsequently added. The reaction mixture is stirred at 25° C. for 12 h. This reaction solution I is transferred to a dropping funnel. 1.5 g (4.4 mmol) of diadamantylchlorophosphine are mixed with 40 ml of THF in a 100 ml three-neck flask. This solution II is cooled to 0° C. Solution I is added dropwise at 0° C. to the solution II. Subsequently, the mixture is heated and stirred under reflux (approximately 60° C.) for 36 h. The reaction solution is concentrated under reduced pressure, and the residue is dissolved with 20 ml of toluene, admixed with 20 ml of water and stirred for 10 min. The phases are separated and the organic phase is dried over a little dry sodium sulfate for 12 h. After filtration, 100 ml of ethanol are added.

The colorless target product crystallizes out within day. It is filtered and dried under reduced pressure.

Yield: 0.25 g (15.3% of theory); M=744.03 g/mol $^{31}$P NMR:(δ[ppm], J[Hz], $CDCl_3$): 17.81 d, J=5.5; 4.75 d, J=5.5

$^{1}$H NMR: (δ[ppm], J[Hz], $CDCl_3$): 1.5–2.0 m (60H); 6.2 t, J=3:1 (1H); 6.6 d,d J=1.5, J=3.6 (1H) 6.9 m (1H); 7.1 m (1H); 7.2 m (2H); 7.8 m (1H)

MS, m/z (%): 744 (3)[$M^+$], 608 (60)[$M^+$-Ad], 442 (2) [$M^+$-$PAd_2$], 301(2)[$PAd_2$], 135 (100) [Ad]

Examples 4–7

General Procedure 1 (GP 1) for Synthesis of Rhodium (I)-NBD or COD Complexes with Cyc-JaPHOS and JaPhOS as Ligands 1 mmol of Rh(NBD)(acac) or Rh(COD) (acac) is dissolved in 10 ml. of THF and cooled to −70° C. 1 mmol of ligand from Example 1–2 dissolved in 40 ml of THF is added dropwise to the rhodium solution within 10 minutes. The solution is heated to room temperature with magnetic stirring and admixed with 120 µl of 54% $HBF_4$ (solution in ether). Subsequently, precipitation is effected using 20 ml of $Et_2O$, followed by filtering and washing with $Et_2O$. The yields are over 90%. The analytical data of the compounds prepared by GP 1 are compiled in Table 1.

TABLE 1

Analytical data of the complexes of Examples 4–8 (NMR[MeOD-d4], δ[ppm], J[Hz], MS Intectra AMD 402, FAB positive using NBA as the matrix)

| Ex. No. | Formula | Yield [%] | $^{31}$P NMR | $^{1}$H NMR | MS, m/z (%): |
|---|---|---|---|---|---|
| 4 | $Rh(I)(Cyc\text{-}JaPHOS)(COD)^{+}BF_4^{-}$<br>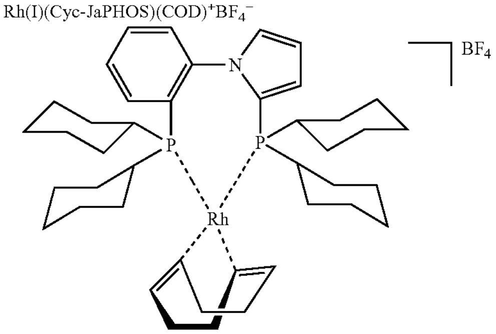 | 94 | 24.4 d,d;<br>$^{2}J_{PP}$ = 24.9;<br>$^{1}J_{PRh}$ = 130.4<br>18.7 d,d;<br>$^{2}J_{PP}$ = 24,9;<br>$^{1}J_{PRh}$ =<br>145.65 | 0.5–2.5 m(Cy;<br>44 H,COD,8H),<br>4.5 bs (1H, COD)<br>4.7bs (1H,COD)<br>4.9 bs (1H, COD)<br>5.8 bs (1H,COD)<br>6.45 d,d,<br>J = 1.59,<br>J = 1.58 (1H)<br>6.9 m (1H)<br>7.2 m (2H)<br>7.5 m (2H)<br>7.9 m (1H) | 746 (100) [Rh(Cyc-JaPHOS)(COD)]$^{+}$;<br>637 (70) [Rh(Cyc-JaPHOS)(COD)]$^{+}$<br>-NBD |
| 5 | $Rh(I)(Cyc\text{-}JaPHOS)(NBD)^{+}BF_4^{-}$<br>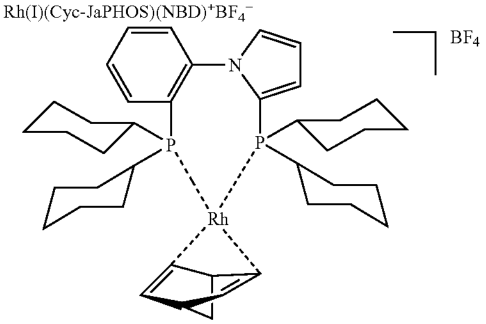 | 90 | 25.1 d of m,<br>$^{1}J_{PRh}$ = 154<br>11.1 d of m<br>$^{1}J_{PRh}$ = 131.8 | 0.8–2.1 m (Cy, 44 H,<br>NBD,2H);<br>3.9 bs (1H, NBD)<br>4.1 bs (1H,NBD)<br>4.8 bs (1H, COD)<br>5.1–5.3<br>m (3H,NBD)<br>6.5 d,d, m(1H)<br>6.9 m (1H)<br>7.2 m (1H)<br>7.5 m (1H)<br>7.9 m (3H) | 730 (100) [Rh(Cyc-JaPHOS)(NBD)]$^{+}$;<br>637 (80) [Rh(Cyc-JaPHOS)(NBD)]$^{+}$<br>-NBD |
| 6 | $Rh(I)(JaPHOS)(COD)^{+}BF_4^{-}$<br>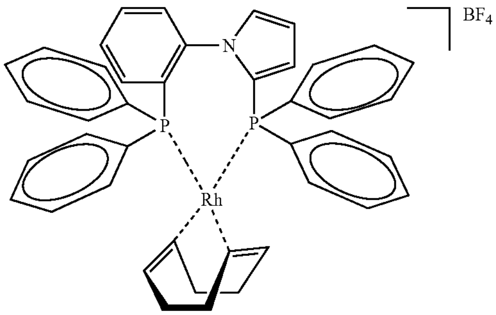 | 93 | 21.3 d,d;<br>$^{2}J_{PP}$ = 37.5;<br>$^{1}J_{PRh}$ =<br>148.43<br>18.1 d,d;<br>$^{2}J_{PP}$ = 37.5;<br>$^{1}J_{PRh}$ = 147.0 | 2.0 m (4H, COD)<br>2.5–2.7m<br>(4H, COD)<br>4.55 m (2H,<br>COD)<br>4.7 m (2H, COD)<br>5.75 m (1H)<br>6.21 m (1H)<br>6.44 m (1H)<br>6.55 m (1H)<br>7.05 m (2H)<br>7.2–7.5 (18H)<br>7.68 d,<br>J = 6.9 (1H)<br>7.69 d,<br>J = 6.9 (1H)<br>7.8 d,<br>J = 7.6 (1H);<br>7.81 d,<br>J = 7.63 (1H) | 722 (100<br>[Rh(Cyc-JaPHOS)(COD)]$^{+}$;<br>614 (75) [Rh(Cyc-JaPHOS)(COD)]$^{+}$<br>-COD |

TABLE 1-continued

Analytical data of the complexes of Examples 4–8 (NMR[MeOD-d4], δ[ppm], J[Hz], MS Intectra AMD 402, FAB positive using NBA as the matrix)

| Ex. No. | Formula | Yield [%] | $^{31}P$ NMR | $^{1}H$ NMR | MS, m/z (%): |
|---|---|---|---|---|---|
| 7 | $Rh(I)(JaPHOS)(NBD)^{+}BF_4^{-}$ 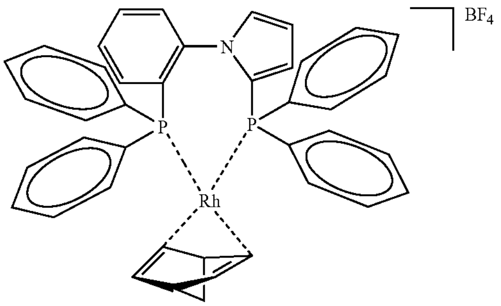 | 91 | 22.7 d,d; $^{2}$Jphd PP = 38.84; $^{1}J_{PRh}$ = 158.14 18.7 d,d; $^{2}J_{PP}$ = 38.84; $^{1}J_{PRh}$ = 156.75 | 1.5 bs (2H, NBD) 4.0 bs (2H, NBD) 4.55 bs (1H, NBD) 4.65 bs (1H, NBD) 5.0 bs (1H, NBD) 5.2 bs (1H, NBD) 5.75 m (1H) 6.2 m (1H) 6.3 m (1H) 6.55 m (1H) 7.05 m (2H) 7.2–7.5 (18H) 7.7 d, J = 6.9 (1H) 7.71 d, J = 6.9 (1H) 7.9 d, J = 7.6 (1H) 7.91 d, J = 7.63 (1H) | 706 (100) $[Rh(JaPHOS)(NBD)]^{+}$; 614 (45) $[Rh(JaPHOS)(COD)]^{+}$-NBD |

Example 8

Hydroformylation Reaction of 1- or cis/trans-2-pentene Using a Rhodium/JaPHOS Catalyst A mixture of 73 mmol of alkene, the corresponding amount of $Rh(acac)(CO)_2$ as a catalyst precursor (0.01 mol % of catalyst, 0.0073 mmol=1.88 mg), the corresponding amount of JaPHOS, 2 ml of isooctane as an internal standard and also 30 ml of anisole as a solvent is reacted in a Parr 100 ml autoclave (with magnetic stirring). The synthesis gas pressure ($H_2$/CO=1:1) is kept constant at the specified value once the working pressure is obtained. After the reaction time, completion of cooling and decompression of the autoclave, the reaction mixture is analyzed by gas chromatography (results see Table 2).

TABLE 2

Hydroformylation results of 1- or cis/trans-2-pentene using a rhodium/JaPHOS catalyst

| Substrate | Rh [mol %] | Rh:JaPHOS [mol/mol] | T [° C.] | P [bar] | T [h] | Yield[a] [%] | n:iso[b] |
|---|---|---|---|---|---|---|---|
| 1-Pentene | 0.01 | 1:5 | 120 | 50 | 6 | 94 | 47:53 |
| 2-Pentene[c] | 0.01 | 1:5 | 120 | 50 | 6 | 54 | 24:76 |
| 2-Pentene[c] | 0.01 | 1:5 | 120 | 25 | 6 | 25 | 39:61 |

TABLE 2-continued

Hydroformylation results of 1- or cis/trans-2-pentene using a rhodium/JaPHOS catalyst

| Substrate | Rh [mol %] | Rh:JaPHOS [mol/mol] | T [° C.] | P [bar] | T [h] | Yield[a] [%] | n:iso[b] |
|---|---|---|---|---|---|---|---|

[a]Yield = 1-hexanal + 2-methylpentanal + 2-ethylbutanal,
[b]n:iso = 1-hexanal:2-methylpentanal + 2-ethylbutanal, [mol:mol]
[c]2-pentene = cis/trans-2-pentene

Example 9

General Procedure for Hydrogenating Olefins by Means of Catalysis Using Rhodium/N-phenylpyrrolylbisphosphine Catalysts from Example 4–7: (GP 3)

0.01 mmol (or less) of the appropriate complex from Example 4–7 is melted in a glass ampule and introduced under argon into a thermostated hydrogenation vessel (equipped with magnetic stirring). Subsequently, 15 ml of methanol and 1 mmol of substrate are added. After gas exchange of argon for hydrogen, the reaction is started by destroying the glass ampule of the precatalyst. During the reaction, the temperature is kept constant at 25° C. and the hydrogen pressure at 1 bar, and the gas consumption is measured using automatic registering apparatus. The time to complete conversion of the substrate is measured. The product is subsequently analyzed by GC. Example see Table 3.

TABLE 3

Hydrogenation results for hydrogenating olefins by means of catalysis using rhodium/N-phenylpyrrolylbisphosphine catalysts

| Precatalyst (mmol) | Substrate (mmol) | t1 | t2 |
|---|---|---|---|
| $Rh(I)(JaPHOS)(COD)^+BF_4^-$ (0.01) | COD[a] (1) | COD→COE[b] 4.7 h | COE→COA[c] 3 d |
| $Rh(I)(JaPHOS)(NBD)^+BF_4^-$ (0.01) | NBD[d] (1) | NBD[d]→NBE[e] 2.5 min | NBE[e]→NBA[f] 40 min |
| $Rh(I)(Cyc\text{-}JaPHOS)(COD)^+BF_4^-$ (0.01) | COD[a] (1) | COD→COE[b] 100 min | COE→COA[c] 10 min |
| $Rh(I)(Cyc\text{-}JaPHOS)(NBD)^+BF_4^-$ (0.0007) | NBD[d] (1) | NBD[d]→NBE[e] 2.5 min | NBE[e]→NBA[f] 40 min |

[a] = 1,4-cyclooctadiene,
[b] = cyclooctene,
[c] = cyclooctane,
[d] = 2,5-norbornadiene,
[e] = 2-norbornene,
[f] = norbornane

What is claimed is:

1. An N-phenylpyrrolebisphosphine of formula I (I)

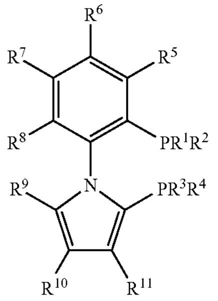

where $R^1$, $R^2$, $R^3$, $R^4$ are selected from the group consisting of aliphatic, cycloaliphatic and aromatic hydrocarbon radicals having from 1 to 25 carbon atoms, and $R^1$ and $R^2$ and/or $R^3$ and $R^4$ may be joined by one or more covalent bonds, $R^5$, $R^6$, $R^7$, $R^8$, $R^9$, $R^{10}$, $R^{11}$ are selected from the group consisting of H, aliphatic, alicyclic, aliphatic-alicyclic, heterocyclic, aliphatic-heterocyclic, aromatic, aromatic-aromatic, and aliphaticaromatic hydrocarbon radicals having from 1 to 50 carbon atoms, and $R^5$ to $R^{11}$ may each be defined identically or differently and be covalently joined together, and each are selected from the group consisting of F, Cl, Br, I, $—Si(CH_3)_3$, $—CF_3$, $—OR^{12}$, $—COR^{12}$, $—CO_2R^{12}$, $—CO_2M$, $—SR^{12}$, $—SO_2R^{12}$, $—SOR^{12}$, $—SO_3R^{12}$, $—SO_3M$, $—SO_2NR^{12}R^{13}$, $NR^{12}R^{13}$, $N^+R^{12}R^{13}R^{13}$, and $N{=}CR^{12}R^{13}$, $NH_2$, where $R^{12}$, $R^{13}$ is selected from the group consisting of H, substituted or unsubstituted aliphatic and aromatic hydrocarbon radicals having from 1 to 25 carbon atoms, each defined identically or differently, and M is selected from the group consisting of alkali metal, alkaline earth metal, ammonium, and phosphonium ion.

2. An N-phenylpyrrolebisphosphine as claimed in claim 1, wherein $R^5$ and $R^6$ together are a fused aromatic in formula II (II)

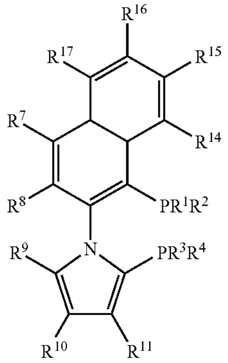

where $R^{14}$, $R^{15}$, $R^{16}$, $R^{17}$ are the same or different and are selected from the group consisting of H, aliphatic, alicyclic, aliphatic-alicyclic, heterocyclic, aliphatic-heterocyclic, aromatic, aromatic-aromatic, aliphatic-aromatic hydrocarbon radicals having from 1 to 50 carbon atoms, F, Cl, Br, I, $—Si(CH_3)_3$, $—CF_3$, $—OR^{12}$, $—COR^{12}$, $—CO_2R^{12}$, $—CO_2M$, $—SR^{12}$, $—SO_2R^{12}$, $—SOR^{12}$, $—SO_3R^{12}$, $—SO_3M$, $—SO_2NR^{12}R^{13}$, $NR^{12}R^{13}$, $N^+R^{12}R^{13}R^{13}$, $N{=}CR^{12}R^{13}$, and $NH_2$, where $R^{12}$, $R^{13}$ are selected from the group consisting of H, substituted or unsubstituted aliphatic and aromatic hydrocarbon radicals having from 1 to 25 carbon atoms, each defined identically or differently, and M is selected from the group consisting of alkali metal, alkaline earth metal, ammonium and phosphonium ion.

3. An N-phenylpyrrolebisphosphine as claimed in claim 1, wherein $R^6$ and $R^7$ together are a fused aromatic in formula III (III)

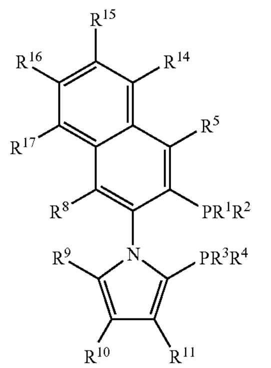

where $R^{14}$, $R^{15}$, $R^{16}$, $R^{17}$ are selected from the group consisting of H, aliphatic, alicyclic, aliphatic-alicyclic, heterocyclic, aliphatic-heterocyclic, aromatic, aromatic-aromatic, aliphatic-aromatic hydrocarbon radicals having from 1 to 50 carbon atoms, F, Cl, Br, I, —$Si(CH_3)_3$, —$CF_3$, —$OR^{12}$, —$COR^{12}$, —$CO^2R^{12}$, —$CO^2M$, —$SR^{12}$, —$SO^2R^{12}$, —$SOR^{12}$, —$SO_3R^{12}$, —$SO^3M$, —$SO_2NR^{12}R^{13}$, $NR^{12}R^{13}$, $NR^{12}R^{13}R^{13}$, $N{=}CR^{12}R^{13}$, and $NH_2$, where $R^{12}$, $R^{13}$ are selected from the group consisting of H, substituted or unsubstituted aliphatic and aromatic hydrocarbon radicals having from 1 to 25 carbon atoms, each defined identically or differently, and M is selected from the group consisting of alkali metal, alkaline earth metal, ammonium, and phosphonium ion.

4. An N-phenylpyrrolebisphosphine as claimed in claim 1, wherein $R^7$ and $R^8$ together are a fused aromatic in formula IV (IV)

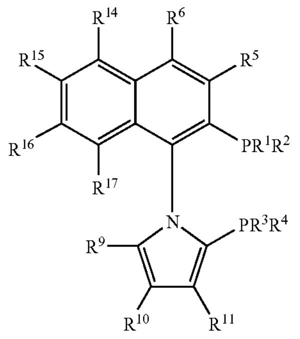

where $R^{14}$, $R^{15}$, $R^{16}$, $R^{17}$ are selected from the group consisting of H, aliphatic, alicyclic, aliphatic-alicyclic, heterocyclic, aliphatic-heterocyclic, aromatic, aromatic-aromatic, aliphatic-aromatic hydrocarbon radicals having from 1 to 50 carbon atoms, F, Cl, Br, I, —$Si(CH^3)^3$, —$CF^3$, —$OR^{12}$, —$COR^{12}$, —$COR_2R^{12}$, —$CO_2M$, —$SR^{12}$, —$SO_2R^{12}$, —$SOR^{12}$, —$SO_3R^{12}$, —$SO_3M$, —$SO_2NR^{12}R^{13}$, $NR^{12}R^{13}$, $N^+R^{12}R^{13}R^{13}$, $N{=}CR^{12}R^{13}$, and $NH_2$, where $R^{12}$, $R^{13}$ are selected from the group consisting of H, substituted or unsubstituted aliphatic and aromatic hydrocarbon radicals having from 1 to 25 carbon atoms, each defined identically or differently, and M is selected from the group consisting of alkali metal, alkaline earth metal, ammonium, and phosphonium ion.

5. An N-phenylpyrrolebisphosphine as claimed in claim 1, wherein $R^9$ and $R^{10}$ together are a fused aromatic in formula V (V)

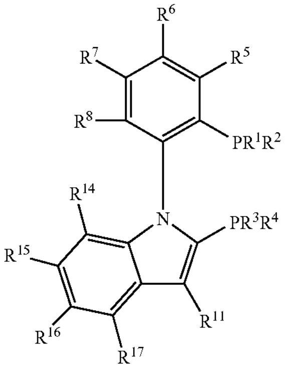

where $R^{14}$, $R^{15}$, $R^{16}$, $R^{17}$ are selected from the group consisting of H, aliphatic, alicyclic, aliphatic-alicyclic, heterocyclic, aliphatic-heterocyclic, aromatic, aromatic-aromatic, aliphatic-aromatic hydrocarbon radicals having from 1 to 50 carbon atoms, F, Cl, Br, I, —$Si(CH_3)_3$, —$CF_3$, —$OR^{12}$, —$COR^{12}$, —$CO_2R^2$, —$CO_2M$, —$SR^{12}$, —$SO_2R^{12}$, —$SOR^{12}$, —$SO_3R^{12}$, —$SO_3M$, —$SO_2NR^{12}R^{13}$, $NR^{12}R^{13}$, $N^+R^{12}R^{13}R^{13}$, $N{=}CR^{12}R^{13}$, and $NH_2$, where $R^{12}$, $R^{13}$ are selected from the group consisting of H, substituted or unsubstituted aliphatic and aromatic hydrocarbon radicals having from 1 to 25 carbon atoms, each defined identically or differently, and M=alkali metal, alkaline earth metal, ammonium, and phosphonium ion.

6. An N-phenylpyrrolebisphosphine as claimed in claim 1, which is chiral.

7. An N-phenylpyrrolebisphosphine as claimed in claim 1, wherein one or more of the radicals $R^1$–$R^4$ or $R^1$ and $R^2$ and/or $R^3$ and $R^4$ together are a chiral radical selected from the group consisting of menthyl, eamphyl, 1,1'-binaphth-2-yl, and hexane-2,5-diyl.

8. An N-phenylpyrrolebisphosphine-metal complex comprising a metal of the 1st, 2nd, 3rd, 4th, 5th, 6th, 7th or 8th transition group of the Periodic Table of the Elements, or an element from the lanthanides and/or actinides and one or more N-phenylpyrrolebisphosphines of formula I

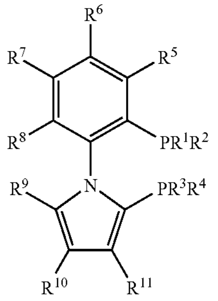

(I)

where $R^1$, $R^2$, $R^3$, $R^4$ are selected from the group consisting of aliphatic, cycloaliphatic and aromatic hydrocarbon radicals having 1 to 25 carbon atoms, $R^5$, $R^6$, $R^7$, $R^8$, $R^9$, $R^{10}$, $R^{11}$ are selected from the group consisting of H, aliphatic, alicyclic, aliphatic-alicyclic, heterocyclic, aliphatic-heterocyclic, aromatic, aromatic-aromatic, and aliphaticaromatic hydrocarbon radicals having from 1 to 50 carbon atoms, and $R^5$ to $R^{11}$ may each be defined identically or differently and be covalently joined together, and each are selected from the group consisting of F, Cl, Br, I, —$Si(CH_3)_3$, —CF, —$OR^{11}$, —$COR^{12}$, —$CO_2R^{12}$, —$CO_2M$, —$SR^{12}$, —$SO_2R^{12}$, —$SOR^{12}$, —$SO_3R^{12}$, —$SO_3M$, —$SO_2NR^{12}R^{13}$, $NR^{12}R^{13}$, $N+R^{12}R^{13}R^{13}$, $N{=}CR^{12}R^{13}$, and $NH_2$, where $R^{12}$, $R^{13}$ are selected from the group consisting of H, substituted or unsubstituted aliphatic and aromatic hydrocarbon radicals having from 1 to 25 carbon atoms, each defined identically or differently, and M is selected from the group consisting of alkali metal, alkaline earth metal, ammonium, and phosphonium ion.

9. An N-phenylpyrrolebisphosphine-metal complex as claimed in claim 8, wherein $R^5$ and $R^6$ together are a fused aromatic in formula II

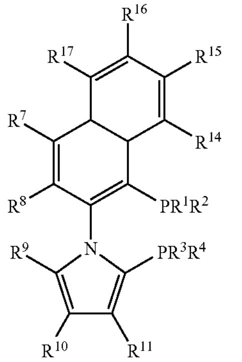

(II)

where $R^{14}$, $R^{15}$, $R^{16}$, $R^{17}$ are selected from the group consisting of H, aliphatic, alicyclic, aliphatic-alicyclic, heterocyclic, aliphatic-heterocyclic, aromatic, aromatic-aromatic, aliphatic-aromatic hydrocarbon radicals having from 1 to 50 carbon atoms, F, Cl, Br, I, —$Si(CH_3)_3$, —$CF_3$, —$OR^{12}$, —$COR^{12}$, —$CO_2R^{12}$, —$CO_2M$, —$SR^{12}$, —$SO_2R^{12}$, —$SO_3R^{12}$, $SO_3M$, —$SO_2NR^{12}R^{13}$, $NR^{12}R^{13}$, $N^+R^{12}R^{13}R^{13}$, $N{=}CR^{12}R^{13}$, and $NH_2$, where $R^{12}$,$R^{13}$ are selected from the group consisting of H, substituted or unsubstituted aliphatic and aromatic hydrocarbon radicals having from 1 to 25 carbon atoms, each defined identically or differently, and M is selected from the group consisting of alkali metal, alkaline earth metal, ammonium, and phosphonium ion and one or more of the radicals $R^1$–$R^4$ or $R^1$and $R^2$ and/or $R^3$ and $R^4$ together are a chiral radical selected from the group consisting of menthyl, camphyl, 1,1'-binaphth-2-yl, and hexane-2,5-diyl.

10. An N-phenylpyrrolebisphosphine-metal complex as claimed in claim 8, wherein $R^6$ and $R^7$ together are a fused aromatic in formula III

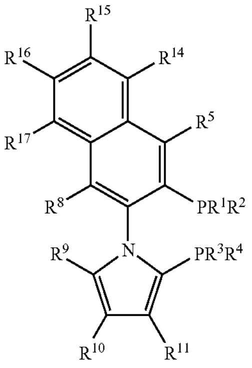

(III)

where $R^{14}$, $R^{15}$, $R^{16}$, $R^{17}$ are selected from the group consisting of H, aliphatic, alicyclic, aliphatic-alicyclic, heterocyclic, aliphatic-heterocyclic, aromatic, aromatic-aromatic, aliphatic-aromatic hydrocarbon radicals having from 1 to 50 carbon atoms, F, Cl, Br, I, —$Si(CH_3)_3$, —$CF_3$, —$OR^{12}$, —$COR^{12}$, —$CO_2R^{12}$, —$CO_2M$, —$SR^{12}$, —$SO_2R^{12}$ , —$SOR^{12}$, —$SO_3R^{12}$, —$SO_3M$, —$SO_2NR^{12}R^{13}$, $NR^{12}R^{13}$, $N^+R^{12}$ $R^{13}R^{13}$, $N{=}CR^{12}R^{13}$, and $NH_2$, where $R^{12}$, $R^{13}$ are selected from the group consisting of H, substituted or unsubstituted aliphatic and aromatic hydrocarbon radicals having from 1 to 25 carbon atoms, each defined identically or differently, and M is selected from the group consisting of alkali metal, alkaline earth metal, ammonium, and phosphonium ion and one or more of the radicals $R^1$–$R^4$ or $R^1$ and $R^2$ and/or $R^3$ and $R^4$ together are a chiral radical selected from the group consisting of menthyl, camphyl, 1,1'-binaphth-2-yl, and hexane-2,5-diyl.

11. An N-phenylpyrrolebisphosphine-metal complex as claimed in claim 8, wherein $R^7$ and $R^8$ together are a fused aromatic in formula IV (IV)

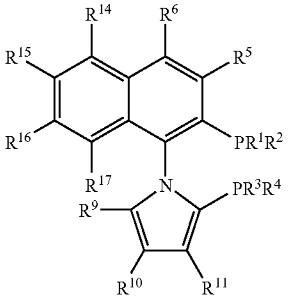

where $R^{14}$, $R^{15}$, $R^{16}$, $R^{17}$ are selected from the group consisting of H, aliphatic, alicyclic, aliphatic-alicyclic, heterocyclic, aliphatic-heterocyclic, aromatic, aromatic-aromatic, aliphatic-aromatic hydrocarbon radicals having from 1 to 50 carbon atoms, F, Cl, Br, I, $—Si(CH_3)_3$, $—CF_3$, $—OR^{12}$, $—COR^{12}$, $—CO_2R^{12}$, $—CO_2M$, $—SR^{12}$, $—SO_2R^{12}$, $—SOR^{12}$, $—SO_3R^{12}$, $—SO_3M$, $—SO_2NR^{12}R^{13}$, $NR^{12}R^{13}$, $N^+R^{12}R^{13}R^{13}$, $N{=}CR^{12}R^{13}$, $NH_2$, where $R^{12}$, $R^{13}$ are selected from the group consisting of H, substituted or unsubstituted aliphatic and aromatic hydrocarbon radicals having from 1 to 25 carbon atoms, each defined identically or differently, and M is selected from the group consisting of alkali metal, alkaline earth metal, ammonium, and phosphonium ion and one or more of the radicals $R^1$–$R^4$ or $R^1$ and $R^2$ and/or $R^3$ and $R^4$ together are a chiral radical selected from the group consisting of menthyl, camphyl, 1,1'-binaphth-2-yl, and hexane-2,5-diyl.

12. An N-phenylpyrrolebisphosphine-metal complex as claimed in claim 8, wherein $R^9$ and $R^{10}$ together are a fused aromatic in formula V (V)

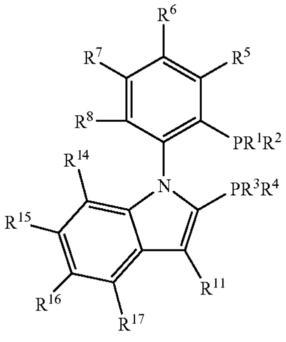

where $R^{14}$, $R^{15}$, $R^{16}$, $R^{17}$ are selected from the group consisting of H, aliphatic, alicyclic, aliphatic-alicyclic, heterocyclic, aliphatic-heterocyclic, aromatic, aromatic-aromatic, aliphatic-aromatic hydrocarbon radicals having from 1 to 50 carbon atoms, F, Cl, Br, I, $—Si(CH_3)_3$, $—CF_3$, $—OR^{12}$, $—COR^{12}$, $—CO_2R^{12}$, $—CO_2M$, $—SR^{12}$, $—SO_2R^{12}$, $—SOR^{12}$, $—SO_3R^{12}$, $—SO_3M$, $—SO_2NR^{12}R^{13}$, $NR^{12}R^{13}$, $N^+R^{12}R^{13}R^{13}$, $N{=}CR^{12}R^{13}$, $NH_2$, where $R^{12}$, $R^{13}$ are selected from the group consisting of H, substituted or unsubstituted aliphatic and aromatic hydrocarbon radicals having from 1 to 25 carbon atoms, each defined identically or differently, and M is selected from the group consisting of alkali metal, alkaline earth metal, ammonium, and phosphonium ion and one or more of the radicals $R^1$–$R^4$ or $R^1$ and $R^2$ and/or $R^3$ and $R^4$ together are a chiral radical selected from the group consisting of menthyl, camphyl, 1,1'-binaphth-2-yl, and hexane-2,5-diyl.

13. An N-phenylpyrrolebisphosphine-metal complex as claimed in claim 8, wherein one or more of the N-phenylpyrrolebisphosphine ligands present in the complex is chiral.

14. An N-phenylpyrrolebisphosphine-metal complex as claimed in claim 8, wherein one or more of the radicals $R^1$–$R^4$ or $R^1$ and $R^2$ and/or $R^3$ and $R^4$ of one or more N-phenylpyrrolebisphosphine ligands present in the complex together are a chiral radical selected from the group consisting of menthyl, camphyl, 1,1'-binaphth-2-yl, and hexane-2,5-diyl.

15. An N-phenylpyrrolebisphosphine-metal complex as claimed in claim 8, wherein the metal is a metal of the 8th transition group of the Periodic Table.

16. A method comprising:

reacting at least one olefin with N-phenylpyrrolebisphosphine as claimed in claim 1, wherein said reacting is selected from the group consisting of hydrogenation, isomerization, carbonylation, carboxylation, hydroformylation, hydrocyanation, cyclopropanation, C—C coupling, oligomerization and polymerization.

17. A method comprising:

reacting at least one olefin with an N-phenylpyrrolebisphosphine-metal complex as claimed in claim 8, wherein said reacting is selected from the group consisting of hydrogenation, isomerization, carbonylation, carboxylation, hydroformylation, hydrocyanation, cyclopropanation, C—C coupling, oligomerization and polymerization.

* * * * *